United States Patent [19]

Chabot-Fletcher et al.

[11] Patent Number: 6,030,811
[45] Date of Patent: Feb. 29, 2000

[54] POLYNUCLEOTIDES ENCODING A HUMAN MYSTROPHIN CLONE, HSABH01

[75] Inventors: Marie Chabot-Fletcher, Phoenixville; Karen M Anderson, West Chester, both of Pa.

[73] Assignee: SmithKline Beecham Corporation, Philadelphia, Pa.

[21] Appl. No.: 08/965,904

[22] Filed: Nov. 7, 1997

Related U.S. Application Data

[60] Provisional application No. 60/030,677, Nov. 13, 1996.

[51] Int. Cl.[7] .......................... C12N 15/12; C12N 15/63; C12N 1/21; C12N 5/00
[52] U.S. Cl. ................. 435/69.4; 435/70.1; 435/325; 435/320.1; 435/243; 436/23.51; 530/399
[58] Field of Search ................................. 435/69.1, 69.4, 435/320.1, 243, 325, 70.1; 536/23.1, 23.5; 530/399

[56] References Cited

PUBLICATIONS

George et al. Macromolecular Sequencing & Synthesis. pp. 127–149, 1988.

Sivasubramanian et al., "Cardiac Myotrophin Exhibits rel/NF–kB Interacting Activity in Vitro", *Journal of Biological Chemistry*, 271(5), pp. 2812–2816 (1996).

Sen et al., "Myotrophin:Purification of a Novel Peptide from Spontaneously Hypertensive Rat Heat That Influences Myocardial Growth", *Journal of Biological Chemistry*, 265(27), pp. 16635–16643 (1990).

Sil et al., "Myotrophin in Human Cardiomyopathic Heart", *Circulation Research*, 73, pp. 98–108 (1993).

Pennica et al., "Isolation of cDNA clones encoding the mouse protein V–1*", *Gene*, 158, pp. 305–306 (1995).

Sawada, K., "Characterization of terminally differentiated cell state by etc.", Accession No. D26326 (1996).

*Primary Examiner*—John Ulm
*Assistant Examiner*—Christine Saoud
*Attorney, Agent, or Firm*—William T. Han; Ratner & Prestia; William T. King

[57] ABSTRACT

A human cDNA encoding human myotrophin and the polypeptide encoded thereby and a procedure for producing such polypeptides by recombinant techniques are disclosed. Also disclosed are methods for utilizing the human myotrophin polynucleotides and polypeptides encoded thereby for the treatment of diseases relating to cellular hypertrophy, among others. Also disclosed are diagnostic assays for detecting diseases related to mutations in the nucleic acid sequences and altered concentrations of the polypeptides.

14 Claims, 2 Drawing Sheets

Figure 1A: Human Myotrophin Nucleotide Sequence, HSABH01

GGCACGAGCCACCGCCTCCTCATCTTCTGCCCGGCCAACCGGCCTGCCCCGCTGCAGTGA

TGTGCGACAAGGAGTTCATGTGGGCCCTGAAAAACGGAGACTTGGATGAGGTGAAAGACT

ATGTGGCCAAGGGAGAAGATGTCAACCGGACACTAGAAGGTGGAAGGAAACCTCTTCATT

ATGCAGCAGATTGTGGGCAGCTTGAAATCCTGGAATTTCTGCTGCTGAAAGGAGCAGATA

TTAATGCTCCAGATAAACATCATATTACTCCTCTTCTGTCTGCTGTCTATGAGGGTCATG

TTTCCTGTGTGAAATTGCTTCTGTCAAAGGGTGCTGATAAGACTGTGAAAGGCCCAGATG

GACTGACCGCCTTTGAAGCCACTGACAACCAGGCAATCAAAGCTCTTCTCCAGTGATGGA

TGGATGGACTGATAACTCCGGAAGAATGACTCTCCTGTGGCCTCACACTGCTGCCTGTCT

GTCTGTCACTCTCTATCTGCCAGCTTCTTCAGCTAAATACTTTAAGAGGGGTGAGGGGAG

AGAGAAATTCATAACAAATCCGACTACCAGAAAAAAAAAAAAAAAAAA

Figure 1B: Deduced Amino Acid Sequence encoded by HSABH01

MCDKEFMWALKNGDLDEVKDYVAKGEDVNRTLEGGRKPLHYAADCGQLEILEFLLLKGAD
INAPDKHHITPLLSAVYEGHVSCVKLLLSKGADKTVKGPDGLTAFEATDNQAIKALLQ

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 588 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:1:

```
GGCACGAGCC ACCGCCTCCT CATCTTCTGC CCGGCCAACC GGCCTGCCCC GCTGCAGTGA    60

TGTGCGACAA GGAGTTCATG TGGGCCCTGA AAAACGGAGA CTTGGATGAG GTGAAAGACT   120

ATGTGGCCAA GGGAGAAGAT GTCAACCGGA CACTAGAAGG TGGAAGGAAA CCTCTTCATT   180

ATGCAGCAGA TTGTGGGCAG CTTGAAATCC TGGAATTTCT GCTGCTGAAA GGAGCAGATA   240

TTAATGCTCC AGATAAACAT CATATTACTC CTCTTCTGTC TGCTGTCTAT GAGGGTCATG   300

TTTCCTGTGT GAAATTGCTT CTGTCAAAGG GTGCTGATAA GACTGTGAAA GGCCCAGATG   360

GACTGACCGC CTTTGAAGCC ACTGACAACC AGGCAATCAA AGCTCTTCTC CAGTGATGGA   420

TGGATGGACT GATAACTCCG GAAGAATGAC TCTCCTGTGG CCTCACACTG CTGCCTGTCT   480

GTCTGTCACT CTCTATCTGC CAGCTTCTTC AGCTAAATAC TTTAAGAGGG GTGAGGGGAG   540

AGAGAAATTC ATAACAAATC CGACTACCAG AAAAAAAAAA AAAAAAA               588
```

(2) INFORMATION FOR SEQ ID NO:2:

(i) SEQUENCE CHARACTERISTICS:
        (A) LENGTH: 118 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Met Cys Asp Lys Glu Phe Met Trp Ala Leu Lys Asn Gly Asp Leu Asp
 1               5                  10                  15

Glu Val Lys Asp Tyr Val Ala Lys Gly Glu Asp Val Asn Arg Thr Leu
             20                  25                  30

Glu Gly Gly Arg Lys Pro Leu His Tyr Ala Ala Asp Cys Gly Gln Leu
         35                  40                  45

Glu Ile Leu Glu Phe Leu Leu Leu Lys Gly Ala Asp Ile Asn Ala Pro
     50                  55                  60

Asp Lys His His Ile Thr Pro Leu Leu Ser Ala Val Tyr Glu Gly His
65                  70                  75                  80

Val Ser Cys Val Lys Leu Leu Leu Ser Lys Gly Ala Asp Lys Thr Val
                 85                  90                  95

Lys Gly Pro Asp Gly Leu Thr Ala Phe Glu Ala Thr Asp Asn Gln Ala
            100                 105                 110

Ile Lys Ala Leu Leu Gln
            115
```

POLYNUCLEOTIDES ENCODING A HUMAN MYSTROPHIN CLONE, HSABH01

This application claims the benefit from U.S. Provisional Application Ser. No. 60/030,677 filed Nov. 13, 1996.

FIELD OF THE INVENTION

This invention relates, in part, to newly identified polynucleotides and polypeptides; variants and derivatives of the polynucleotides and polypeptides; processes for making the polynucleotides and the polypeptides, and their variants and derivatives; agonists and antagonists of the polypeptides; and uses of the polynucleotides, polypeptides, variants, derivatives, agonists and antagonists. In particular, in these and in other regards, the invention relates to polynucleotides of human myotrophin, hereinafter referred to as "HSABH01".

BACKGROUND OF THE INVENTION

Myotrophin is a soluble 12 kilodalton protein isolated from hypertrophied hearts of spontaneously hypertensive rats and dilated cardiomyopathic human hearts. Myotrophin, when added to neonatal rat myocytes maintained in culture, accelerates myocardial cell growth and increases the number of sarcomeres and gap junction formation. Sen et al., *J. Biol. Chem.* 1990, 265:16635–16643.

The myotrophin gene is expressed in various rat tissues. Sivasubramanian et al., *J. Biol. Chem.* 1996, 271(5):2812–2816. Transcripts were found to be most abundant in brain and least in skeletal muscle compared to other tissues. Based upon its ubiquitous nature, it has been suggested that the myotrophin proteins may have an important role in the basic functions of various tissues. Sivasubramanian et al., *J. Biol. Chem.* 1996,271(5):2812-2816.

Analysis of the primary structure of the rat myotrophin protein has revealed a homology between one of the ankyrin repeats of myotrophin and the I$\kappa$B$\alpha$/rel ankyrin repeats. Sivasubramanian et al., *J. Biol. Chem.* 1996, 271(5):2812–2816. Putative consensus phosphorylation sites have been identified for protein kinase C and casein kinase II in myotrophin protein, which were also observed in I$\kappa$B$\alpha$ proteins. The significance of these homologies was confirmed in vitro by gel shift assays which showed that recombinant myotrophin has the ability to interact with NF-$\kappa$B/rel proteins. Sivasubramanian et al., *J. Biol. Chem.* 1996, 271(5):2812–2816.

NF-$\kappa$B/rel proteins have been shown to be involved in the rapid induction of genes whose products are important in immune responses, inflammation and cell proliferation. NF-$\kappa$B is rapidly translocated from the cytoplasm to the nucleus in response to extracellular signals. It is believed that myotrophin is a component of this rapid response system and may be involved in the regulation of expression of hypertrophy-specific genes in the myocardium and I other tissues.

Clearly there is a need for identification and characterization of the human myotrophin gene, the modulation of which may play a role in preventing, ameliorating or correcting dysfunctions or diseases relating to cellular hypertrophy.

SUMMARY OF THE INVENTION

Toward these ends, and others, it is an object of the present invention to provide polypeptides, inter alia, that have been identified as novel human myotrophin, also referred to herein as polypeptides or proteins encoded by HSABH01.

It is a further object of the invention, moreover, to provide polynucleotides that encode human myotrophin.

In a particularly preferred embodiment of this aspect of the invention, the polynucleotide comprises the region encoding human myotrophin in the sequence set out in FIG. 1A.

In accordance with this aspect of the invention, there are provided isolated nucleic acid molecules encoding human myotrophin, including mRNAs, cDNAs, genomic DNAs and fragments and, in further embodiments of this aspect of the invention, biologically, diagnostically, clinically or therapeutically useful variants, analogs or derivatives thereof, including fragments of the variants, analogs and derivatives.

Among the particularly preferred embodiments of this aspect of the invention are naturally occurring allelic variants of human myotrophin.

In accordance with another aspect of the present invention, there are provided methods of screening for compounds which bind to and induce or inhibit expression of the polynucleotides of the present invention.

It is another object of the invention to provide a process for producing the aforementioned polypeptides, polypeptide fragments, variants and derivatives, fragments of the variants and derivatives, and analogs of the foregoing. In a preferred embodiment of this aspect of the invention there are provided methods for producing human myotrophin polypeptides comprising culturing host cells having expressibly incorporated therein an exogenously-derived human myotrophin-encoding polynucleotide under conditions for expression of human myotrophin in the host and then recovering the expressed polypeptide. In a preferred embodiment, the myotrophin-encoding polynucleotide is HSABH01.

In accordance with another object the invention, there are provided products, compositions, processes and methods that utilize the aforementioned polypeptides and polynucleotides for research, biological, clinical and therapeutic purposes, inter alia.

In accordance with certain preferred embodiments of this aspect of the invention, there are provided products, compositions and methods, inter alia, for, among other things: assessing human myotrophin expression in cells by determining human myotrophin polypeptides or human myotrophin-encoding mRNA; assaying genetic variation and aberrations, such as defects, in human myotrophin genes; and administering a human myotrophin polynucleotide or polypeptide encoded thereby to an organism to augment myotrophin function or remediate myotrophin dysfunction.

In accordance with still another embodiment of the present invention, there is provided a process of using such activating compounds to stimulate expression of the human myotrophin gene of the present invention for the treatment of conditions related to the under-expression of myotrophin.

In accordance with another aspect of the present invention, there is provided a process of using such inhibiting compounds for treating conditions associated with over-expression of the human myotrophin gene.

In accordance with yet another aspect of the present invention, there is provided non-naturally occurring synthetic, isolated and/or recombinant polypeptides encoded by HSABH01 or a fragment thereof which are fragments, consensus fragments and/or sequences having conservative amino acid substitutions of at least one ankyrin repeat of myotrophin which is homologous to the I$\kappa$B family of proteins.

In accordance with still another aspect of the present invention, there are provided synthetic or recombinant human myotrophin polypeptides, conservative substitutions and derivatives thereof, antibodies thereto, and anti-idiotype antibodies that can be useful as potential modulators of human myotrophin function by binding to ligands or modulating ligand binding due to their expected biological properties. These compositions may be used in diagnostic, therapeutic and/or research applications.

It is still another object of the present invention to provide synthetic, isolated or recombinant polypeptides which are designed to inhibit or mimic human, myotrophin or fragments thereof.

In accordance with certain preferred embodiments of this and other aspects of the invention, there are provided probes that hybridize to human myotrophin sequences.

In certain additional preferred embodiments of this aspect of the invention, there are provided antibodies against polypeptides encoded by HSABH01 or fragments thereof.

In accordance with another aspect of the present invention, there are provided human myotrophin agonists. Among preferred agonists are molecules that mimic human myotrophin and elicit or augment myotrophin-induced responses.

In accordance with yet another aspect of the present invention, there are provided human myotrophin antagonists. Among preferred antagonists are those which inhibit expression of the human myotrophin gene of the present invention. Also among preferred antagonists are molecules that bind to or interact with human myotrophin encoded by HSABH01 so as to inhibit one or more effects of human myotrophin.

In a further aspect of the invention, there are provided compositions comprising a human myotrophin polynucleotide or polypeptide encoded by HSABH01 or a fragment thereof for administration to cells in vitro, to cells ex vivo and to cells in vivo, or to a multicellular organism. In certain particularly preferred embodiments of this aspect of the invention, the compositions comprise the HSABH01 polynucleotide for expression of a human myotrophin polypeptide in a host organism for treatment of disease. Particularly preferred in this regard is expression in a human patient for treatment of a dysfunction associated with aberrant endogenous activity of myotrophin.

Other objects, features, advantages and aspects of the present invention will become apparent to those of skill in the art from the following description. It should be understood, however, that the following description and the specific examples, while indicating preferred embodiments of the invention, are given by way of illustration only. Various changes and modifications within the spirit and scope of the disclosed invention will become readily apparent to those skilled in the art from reading the following description and from reading the other parts of the present disclosure.

BRIEF DESCRIPTION OF THE DRAWINGS

The following drawings depict certain embodiments of the invention. They are illustrative only and do not limit the invention otherwise disclosed herein.

FIGS. 1A and 1B shows the nucleotide and deduced amino acid sequence of human myotrophin. FIG. 1A provides the nucleic acid sequence of human myotrophin, also referred to herein as HSABH01, SEQ ID NO: 1. FIG. 1B provides the deduced amino acid sequence, SEQ ID NO: 2, encoded by HSABH01.

GLOSSARY

The following illustrative explanations are provided to facilitate understanding of certain terms used frequently herein, particularly in the examples. The explanations are provided as a convenience and are not meant to limit the invention.

"Digestion" of DNA refers to catalytic cleavage of a DNA with an enzyme such as, but not limited to, a restriction enzyme that acts only at certain sequences in the DNA. The various restriction enzymes referred to herein are commercially available and their reaction conditions, cofactors and other requirements for use are known and routine to the skilled artisan.

For analytical purposes, typically, 1 microgram of plasmid or DNA fragment is digested with about 2 units of enzyme in about 20 microliters of reaction buffer. For the purpose of isolating DNA fragments for plasmid construction, typically 5 to 50 micrograms of DNA are digested with 20 to 250 units of enzyme in proportionately larger volumes.

Appropriate buffers and substrate amounts for particular restriction enzymes are described in standard laboratory manuals, such as those referenced below, and they are specified by commercial suppliers.

Incubation times of about 1 hour at 37° C. are ordinarily used, but conditions may vary in accordance with standard procedures, the supplier's instructions and the particulars of the reaction. After digestion, reactions may be analyzed, and fragments may be purified by electrophoresis through an agarose or polyacrylamide gel, using well known methods that are routine for those skilled in the art.

"Genetic element" generally means a polynucleotide comprising a region that encodes a polypeptide or a region that regulates replication, transcription or translation or other processes important to expression of the polypeptide in a host cell, or a polynucleotide comprising both a region that encodes a polypeptide and a region operably linked thereto that regulates expression.

Genetic elements may be comprised within a vector that replicates as an episomal element; that is, as a molecule physically independent of the host cell genome. They may be comprised within mini-chromosomes, such as those that arise during amplification of transfected DNA by methotrexate selection in eukaryotic cells. Genetic elements also may be comprised within a host cell genome, not in their natural state but, rather, following manipulation such as isolation, cloning and introduction into a host cell in the form of purified DNA or in a vector, among others.

"Isolated" means altered "by the hand of man" from its natural state; i.e., that, if it occurs in nature, it has been changed or removed from its original environment, or both.

For example, a naturally occurring polynucleotide or a polypeptide naturally present in a living animal in its natural state is not "isolated," but the same polynucleotide or polypeptide separated from the coexisting materials of its natural state is "isolated", as the term is employed herein. For example, with respect to polynucleotides, the term isolated means that it is separated from the chromosome and cell in which it naturally occurs.

As part of or following isolation, such polynucleotides can be joined to other polynucleotides, such as DNAs, for mutagenesis, to form fusion proteins, and for propagation or expression in a host, for instance. The isolated polynucleotides, alone or joined to other polynucleotides such as vectors, can be introduced into host cells, in culture or in whole organisms. Introduced into host cells in culture or in whole organisms, such DNAs still would be isolated, as the term is used herein, because they would not be in their naturally occurring form or environment. Similarly, the polynucleotides and polypeptides may occur in a composition, such as a media, formulations, solutions for introduction of polynucleotides or polypeptides, for example, into cells, compositions or solutions for chemical or enzymatic reactions, for instance, which are not naturally occurring compositions, and, therein remain isolated polynucleotides or polypeptides within the meaning of that term as it is employed herein.

"Ligation" refers to the process of forming phosphodiester bonds between two or more polynucleotides, which most often are double stranded DNAs. Techniques for ligation are well known to the art and protocols for ligation are described in standard laboratory manuals and references, such as, for instance, Sambrook et al., MOLECULAR CLONING, A LABORATORY MANUAL, 2nd Ed.; Cold Spring Harbor Laboratory Press, Cold Spring Harbor, N.Y., 1989, hereinafter referred to as Sambrook et al.

"Oligonucleotide(s)" refers to relatively short polynucleotides. Often the term refers to single-stranded deoxyribonucleotides, but it can refer as well to single-or double-stranded ribonucleotides, RNA:DNA hybrids and double-stranded DNAs, among others.

Oligonucleotides, such as single-stranded DNA probe oligonucleotides, often are synthesized by chemical methods, such as those implemented on automated oligonucleotide synthesizers. However, oligonucleotides can be made by a variety of other methods, including in vitro recombinant DNA-mediated techniques and by expression of DNAs in cells and organisms.

Initially, chemically synthesized DNAs typically are obtained without a 5' phosphate. The 5' ends of such oligonucleotides are not substrates for phosphodiester bond formation by ligation reactions that employ DNA ligases typically used to form recombinant DNA molecules. Where ligation of such oligonucleotides is desired, a phosphate can be added by standard techniques, such as those that employ a kinase and ATP.

The 3' end of a chemically synthesized oligonucleotide generally has a free hydroxyl group and, in the presence of a ligase, such as T4 DNA ligase, will readily form a phosphodiester bond with a 5' phosphate of another polynucleotide, such as another oligonucleotide. As is well known, this reaction can be prevented selectively, where desired, by removing the 5' phosphates of the other polynucleotide(s) prior to ligation.

"Plasmids" are genetic elements that are stably inherited without being a part of the chromosome of their host cell. They may be comprised of DNA or RNA and may be linear or circular. Plasmids code for molecules that ensure their replication and stable inheritance during cell replication and may encode products of considerable medical, agricultural and environmental importance. For example, they code for toxins that greatly increase the virulence of pathogenic bacteria. They can also encode genes that confer resistance to antibiotics. Plasmids are widely used in molecular biology as vectors used to clone and express recombinant genes. Plasmids generally are designated herein by a lower case p preceded and/or followed by capital letters and/or numbers, in accordance with standard naming conventions that are familiar to those of skill in the art. Starting plasmids disclosed herein are either commercially available, publicly available, or can be constructed from available plasmids by routine application of well known, published procedures. Many plasmids and other cloning and expression vectors that can be used in accordance with the present invention are well known and readily available to those of skill in the art. Moreover, those of skill readily may construct any number of other plasmids suitable for use in the invention. The properties, construction and use of such plasmids, as well as other vectors, in the present invention will be readily apparent to those of skill from the present disclosure.

"Polynucleotide(s)" generally refers to any polyribonucleotide or polydeoxribonucleotide, which may be unmodified RNA or DNA or modified RNA or DNA. Thus, for instance, polynucleotides as used herein refers to, among others, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded or, more typically, double-stranded or a mixture of single- and double-stranded regions.

In addition, polynucleotide as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide.

As used herein, the term polynucleotide includes DNAs or RNAs as described above that contain one or more modified bases. Thus, DNAs or RNAs with backbones modified for stability or for other reasons are polynucleotides as that term is intended herein. Moreover, DNAs or RNAs comprising unusual bases, such as inosine, or modified bases, such as tritylated bases, to name just two examples, are polynucleotides as the term is used herein.

It will be appreciated that a great variety of modifications have been made to DNA and RNA that serve many useful purposes known to those of skill in the art. The term polynucleotide, as it is employed herein, embraces such chemically, enzymatically or metabolically modified forms of polynucleotides, as well as the chemical forms of DNA and RNA characteristic of viruses and cells, including inter alia simple and complex cells.

"Polypeptides", as used herein, includes all polypeptides as described below. The basic structure of polypeptides is well known and has been described in innumerable textbooks and other publications in the art. In this context, the term is used herein to refer to any peptide or protein comprising two or more amino acids joined to each other in a linear chain by peptide bonds. As used herein, the term refers to both short chains, which also commonly are referred to in the art as peptides, oligopeptides and oligomers, for example, and to longer chains, which generally are referred to in the art as proteins, of which there are many types.

It will be appreciated that polypeptides often contain amino acids other than the 20 amino acids commonly referred to as the 20 naturally occurring amino acids, and that many amino acids, including the terminal amino acids, may be modified in a given polypeptide, either by natural processes, such as processing and other post-translational modifications, or by chemical modification techniques which are well known to the art. Even the common modifications that occur naturally in polypeptides are too numerous to list exhaustively here, but they are well described in basic texts and in more detailed monographs, as well as in a voluminous research literature, and thus are well known to those of skill in the art.

Among the known modifications which may be present in polypeptides of the present invention are, to name an illustrative few, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as, for instance PROTEINS—STRUCTURE AND MOLECULAR PROPERTIES, 2nd Ed., T. E. Creighton, W. H. Freeman and Company, New York, 1993. Many detailed reviews are available on this subject, such as, for example, those provided by Wold, F., Posttranslational Protein Modifications: Perspectives and Prospects, pages 1–12 in POST-TRANSLATIONAL COVALENT MODIFCATION OF PROTEINS, B. C. Johnson, Ed., Academic Press, New York, 1983; Seifter et al., "Analysis for protein modifications and nonprotein cofactors", Meth. Enzymol., 1990, 182:626–646 and Rattan et al., "Protein Synthesis: Posttranslational Modifications and Aging", Ann. N. Y. Acad. Sci., 1992, 663: 48–62.

It will be appreciated, as is well known and as noted above, that polypeptides are not always entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well.

Modifications can occur anywhere in a polypeptide, including the peptide backbone, the amino acid side-chains and the amino or carboxyl termini. In fact, blockage of the amino or carboxyl group in a polypeptide, or both, by a covalent modification, is common in naturally occurring and synthetic polypeptides and such modifications may be present in polypeptides of the present invention, as well. For instance, the amino terminal residue of polypeptides made in E. coli, prior to processing, almost invariably will be N-formylmethionine.

The modifications that occur in a polypeptide often will be a function of how it is made. For polypeptides made by expressing a cloned gene in a host, for instance, the nature and extent of the modifications in large part will be determined by the host cell's posttranslational modification capacity and the modification signals present in the polypeptide amino acid sequence. For instance, as is well known, glycosylation often does not occur in bacterial hosts such as E. coli. Accordingly, when glycosylation is desired, a polypeptide should be expressed in a glycosylating host, generally a eukaryotic cell. Insect cells often carry out the same posttranslational glycosylations as mammalian cells and, for this reason, insect cell expression systems have been developed to express efficiently mammalian proteins having the native patterns of glycosylation, inter alia. Similar considerations apply to other modifications.

It will be appreciated that the same type of modification may be present in the same or varying degrees at several sites in a given polypeptide. Also, a given polypeptide may contain many types of modifications.

In general, as used herein, the term polypeptide encompasses all such modifications, particularly those that are present in polypeptides synthesized by expressing a polynucleotide in a host cell.

"Variant(s)" of polynucleotides or polypeptides, as the term is used herein, are polynucleotides or polypeptides that differ from a reference polynucleotide or polypeptide, respectively. Variants in this sense are described below and elsewhere in the present disclosure in greater detail.

For example, variants include polynucleotides that differ in nucleotide sequence from another, reference polynucleotide. Generally, differences are limited so that the nucleotide sequences of the reference and the variant are closely similar overall and, in many regions, identical. Changes in the nucleotide sequence of the variant may be silent. That is, they may not alter the amino acids encoded by the polynucleotide. Where alterations are limited to silent changes of this type, a variant will encode a polypeptide with the same amino acid sequence as the reference. Also as noted below, changes in the nucleotide sequence of the variant may alter the amino acid sequence of a polypeptide encoded by the reference polynucleotide. Such nucleotide changes may result in amino acid substitutions, additions, deletions, fusions and truncations in the polypeptide encoded by the reference sequence, as discussed below.

Variants also include polypeptides that differ in amino acid sequence from another, reference polypeptide. Generally, differences are limited so that the sequences of the reference and the variant are closely similar overall and, in many regions, identical. A variant and reference polypeptide may differ in amino acid sequence by one or more substitutions, additions, deletions, fusions and truncations, which may be present in any combination.

"Fusion protein" as the term is used herein, is a protein encoded by two, often unrelated, fused genes or fragments thereof. EP-A-O 464 533 (Canadian counterpart 2045869) discloses fusion proteins comprising various portions of constant region of immunoglobin molecules together with another human protein or part thereof. In many cases, employing an immunoglobulin Fc region as a part of a fusion protein is advantageous for use in therapy and diagnosis resulting in, for example, improved pharmacokinetic properties (EP-A 0232 262). On the other hand, for some uses it would be desirable to be able to delete the Fc part after the fusion protein has been expressed, detected and purified. Accordingly, it may be desirable to link the components of the fusion protein with a chemically or enzymatically cleavable linking region. This is the case when the Fc portion proves to be a hindrance to use in therapy and diagnosis, for example, when the fusion protein is to be used as an antigen for immunizations. In drug discovery, for example, human proteins, such as, shIL5-α have been fused with Fc portions for use in high-throughput screening assays to identify antagonists of hIL-5. See, D. Bennett et al.,

*Journal of Molecular Recognition,* 1995, 8:52–58, and K. Johanson et al., *The Journal of Biological Chemistry,* 1995, 270(16):9459–9471.

Thus, this invention also relates to genetically engineered soluble fusion proteins comprised of human myotrophin, or a portion thereof, and of various portions of the constant regions of heavy or light chains of immunoglobulins of various subclasses (IgG, IgM, IgA, IgE). Preferred as an immunoglobulin is the constant part of the heavy chain of human IgG, particularly IgG1, where fusion takes place at the hinge region. In a particular embodiment, the Fc part can be removed simple by incorporation of a cleavage sequence which can be cleaved with blood clotting factor Xa. Furthermore, this invention relates to processes for the preparation of these fusion proteins by genetic engineering, and to the use thereof for diagnosis and therapy. A further aspect of the invention also relates to polynucleotides encoding such fusion proteins.

"Binding molecules" refer to molecules, including ligands, that specifically bind to or interact with polypeptides encoded by the gene of the present invention. Such binding molecules are a part of the present invention. Binding molecules may also be non-naturally occurring, such as antibodies and antibody-derived reagents that bind specifically to polypeptides of the invention.

As known in the art, "similarity" between two polypeptides is determined by comparing the amino acid sequence and its conserved amino acid substitutes of one polypeptide to the sequence of a second polypeptide. Moreover, also known in the art is "identity" which means the degree of sequence relatedness between two polypeptide or two polynucleotide sequences as determined by the identity of the match between two strings of such sequences. Both identity and similarity can be readily calculated (COMPUTATIONAL MOLECULAR BIOLOGY, Lesk, A. M., ed., Oxford University Press, New York, 1988; BIOCOMPUTING: INFORMATICS AND GENOME PROJECTS, Smith, D. W., ed., Academic Press, New York, 1993; COMPUTER ANALYSIS OF SEQUENCE DATA, PART I, Griffin, A.M., and Griffin, H. G., eds., Humana Press, New Jersey, 1994; SEQUENCE ANALYSIS IN MOLECULAR BIOLOGY, von Heinje, G., Academic Press, 1987; and SEQUENCE ANALYSIS PRIMER, Gribskov, M. and Devereux, J., eds., M Stockton Press, New York, 1991). While there exist a number of methods to measure identity and similarity between two polynucleotide or polypeptide sequences, the terms "identity" and "similarity" are well known to skilled artisans (Carillo, H., and Lipton, D., SIAM *J. Applied Math.,* 1988, 48:1073). Methods commonly employed to determine identity or similarity between two sequences include, but are not limited to, those disclosed in Guide to Huge Computers, Martin J. Bishop, ed., Academic Press, San Diego, 1994, and Carillo, H., and Lipton, D., SIAM J. Applied Math., 1988, 48:1073. Preferred methods to determine identity are designed to give the largest match between the two sequences tested. Methods to determine identity and similarity are codified in computer programs. Preferred computer program methods to determine identity and similarity between two sequences include, but are not limited to, GCG program package (Devereux, J., et al., *Nucleic Acids Research,* 1984, 12(1):387), BLASTP, BLASTN, and FASTA (Atschul, S. F. et al., *J. Molec. Biol.,* 1990, 215:403).

DETAILED DESCRIPTION OF THE INVENTION

The present invention relates to novel human myotrophin polynucleotides and polypeptides encoded thereby, among other things, as described in greater detail below. In particular, the invention relates to polynucleotides of novel human myotrophin. The invention relates especially to HSABH01 having the nucleotide and deduced amino acid sequences set out in FIGS. 1A and 1B.

Polynucleotides

In accordance with one aspect of the present invention, there are provided isolated polynucleotides which encode human myotrophin polypeptide having the deduced amino acid sequence of FIG. 1B).

Using the information provided herein, such as the polynucleotide sequence set out in FIG. 1A, a polynucleotide of the present invention encoding human myotrophin may be obtained using standard cloning and screening procedures, such as those for cloning cDNAs using mRNA from human cells as starting material. Illustrative of the invention, the polynucleotide set out in FIG. 1A was identified in a cDNA library derived from human HSA172 cells using the nucleotide sequence of rat myotrophin.

HSABH01 of the invention is structurally related to myotrophin proteins from other species. There is 96.4% identity in a 523 base pair overlap between the human and rat myotrophin sequences. The cDNA sequence of HSABH01 is set out in FIG. 1A and also as SEQ ID NO: 1. The human myotrophin cDNA depicted in FIG. 1 is characterized by a relatively short 5' untranslated region followed by an open reading frame from nucleotide 60 to 416. Longer clones have also been identified which contain approximately 150 additional basepairs in the 5' untranslated region. The 3' untranslated region contains a poly A tail and lacks ATTTA repeats, thus indicative of a stable mRNA.

Polynucleotides of the present invention may be in the form of RNA, such as mRNA, or in the form of DNA, including, for instance, cDNA and genomic DNA obtained by cloning or produced by chemical synthetic techniques or by a combination thereof. The DNA may be double-stranded or single-stranded. Single-stranded DNA may be the coding strand, also known as the sense strand, or it may be the non-coding strand, also referred to as the antisense strand.

The coding sequence which encodes the polypeptide may be identical to the coding sequence of the polynucleotide shown in FIG. 1A, SEQ ID NO: 1. It also may be a polynucleotide with a different sequence, which, as a result of the redundancy (degeneracy) of the genetic code, also encodes the polypeptide of FIG. 1B, SEQ ID NO: 2.

Polynucleotides of the present invention which encode the polypeptide of FIG. 1B may include, but are not limited to, the coding sequence for the mature polypeptide, by itself; the coding sequence for the mature polypeptide and additional coding sequences; and the coding sequence of the mature polypeptide, with or without the aforementioned additional coding sequences, together with additional, non-coding sequences. Examples of additional coding sequences include, but are not limited to, sequences encoding a leader or secretory sequence, such as a preprotein, or proprotein or preproprotein sequence. Examples of additional noncoding sequences include, but are not limited to, introns and non-coding 5' and 3' sequences, such as the transcribed, non-translated sequences that play a role in transcription, and mRNA processing, including splicing and polyadenylation signals, for example, for ribosome binding and stability of mRNA. Coding sequences which provide additional functionalities may also be incorporated into the polypeptide. Thus, for instance, the polypeptide may be fused to a marker sequence, such as a peptide, which facilitates purification of the fused polypeptide. In certain preferred embodiments of this aspect of the invention, the marker sequence is a hexa-histidine peptide, such as the tag provided in the pQE vector (Qiagen, Inc.). As described in Gentz et al., *Proc. Natl. Acad. Sci., USA,* 1989, 86:821–824, for instance, hexa-histidine provides for convenient purification of the fusion protein. In another embodiment, the HA tag may serve as a marker sequence. The HA tag corresponds to an epitope derived of influenza hemagglutinin protein, which has been described by Wilson et al., *Cell,* 1984, 37:767, for instance. Many other such tags are commercially available.

In accordance with the foregoing, the term "polynucleotide encoding a polypeptide" as used herein encompasses polynucleotides which include, by virtue of the redundancy of the genetic code, any sequence encoding a polypeptide of the present invention, particularly the polypeptide encoded by HSABH01 having the amino acid sequence set out in FIG. 1B. The term also encompasses polynucleotides that include a single continuous region or discontinuous regions encoding the polypeptide (for example, interrupted by introns) together with additional regions, that also may contain coding and/or non-coding sequences.

The present invention further relates to variants of the herein above described polynucleotides which encode for fragments, analogs and derivatives of the polypeptide having the deduced amino acid sequence of FIG. 1B. A variant of the polynucleotide may be a naturally occurring variant such as a naturally occurring allelic variant, or it may be a variant that is not known to occur naturally. Such non-naturally occurring variants of the polynucleotide may be made by mutagenesis techniques, including those applied to polynucleotides, cells or organisms.

Among variants in this regard are variants that differ from the aforementioned polynucleotides by nucleotide substitutions, deletions or additions. The substitutions, deletions or additions may involve one or more nucleotides. The variants may be altered in coding or non-coding regions or both. Alterations in the coding regions may produce conservative or non-conservative amino acid substitutions, deletions or additions.

Among the particularly preferred embodiments of the invention in this regard are polynucleotides encoding polypeptides having the amino acid sequence set out in FIG. 1B, SEQ ID NO:2; variants, analogs, derivatives and fragments thereof, and fragments of the variants, analogs and derivatives.

Further particularly preferred in this regard are polynucleotides encoding human myotrophin variants, analogs, derivatives and fragments, and variants, analogs and derivatives of the fragments, which have the amino acid sequence of the polypeptide of FIG. 1B in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of the human myotrophin. Also especially preferred in this regard are conservative substitutions. Most highly preferred are polynucleotides encoding polypeptides having the amino acid sequence of FIG. 1, without substitutions such as HSABH01.

Further preferred embodiments of the invention are polynucleotides that are at least 97% identical to HSABH01, and polynucleotides which are complementary to such polynucleotides. Furthermore, those (with at least 98% identity are highly preferred and those with at least 99% are the most preferred.

Particularly preferred embodiments in this respect, moreover, are polynucleotides which encode polypeptides which retain substantially the same biological function or activity as the mature polypeptide encoded by the cDNA of FIG. 1A.

The present invention further relates to polynucleotides that hybridize to the herein above-described sequences. In this regard, the present invention especially relates to polynucleotides which hybridize under stringent conditions to the herein above-described polynucleotides. As herein used, the term "stringent conditions" means hybridization will occur only if there is at least 95% and preferably at least 97% identity between the sequences.

As discussed additionally herein regarding polynucleotide assays of the invention, for instance, polynucleotides of the invention as discussed above, may be used as hybridization probes for cDNA and genomic DNA, to isolate full-length cDNAs and genomic clones encoding human myotrophin and to isolate cDNA and genomic clones of other genes that have a high sequence similarity to the human myotrophin gene. Such probes generally will comprise at least 15 nucleotides. Preferably, such probes will have at least 30 nucleotides and may have at least 50 nucleotides. Particularly preferred probes will range between 30 and 50 nucleotides.

For example, the coding region of the human myotrophin gene may be isolated by screening using the known DNA sequence to synthesize an oligonucleotide probe. A labeled oligonucleotide having a sequence complementary to that of a gene of the present invention is then used to screen a library of human cDNA, genomic DNA or mRNA to determine the members of the library to which the probe hybridizes to.

The polynucleotides and polypeptides of the present invention may be employed as research reagents and materials for discovery of treatments and diagnostics to human disease, as further discussed herein relating to polynucleotide assays.

The polynucleotides may encode a polypeptide which is the mature protein plus additional amino or carboxyl-terminal amino acids, or amino acids interior to the mature polypeptide (when the mature form has more than one polypeptide chain, for instance). Such sequences may play a role in processing of a protein from precursor to a mature form, may facilitate protein trafficking, may prolong or shorten protein half-life or may facilitate manipulation of a protein for assay or production, among other things. As generally is the case in situ, the additional amino acids may be processed away from the mature protein by cellular enzymes.

A precursor protein, having the mature form of the polypeptide fused to one or more prosequences may be an inactive form of the polypeptide. When prosequences are removed such inactive precursors generally are activated. Some or all of the prosequences may be removed before activation. Generally, such precursors are called proproteins.

In sum, a polynucleotide of the present invention may encode a mature protein, a mature protein plus a leader sequence (which may be referred to as a preprotein), a precursor of a mature protein having one or more prosequences which are not the leader sequences of a preprotein, or a preproprotein, which is a precursor to a proprotein, having a leader sequence and one or more prosequences, which generally are removed during processing steps that produce active and mature forms of the polypeptide.

Polypeptides

The present invention further relates to polypeptides encoded by HSABH01 having the deduced amino acid sequence of FIG. 1B, SEQ ID NO: 2. The DNA sequence, SEQ ID NO: 1 was translated into this predicted protein sequence the using Lasergene software package (DNAStar, Madison, Wis.).

The invention also relates to fragments, analogs and derivatives of these polypeptides. The terms "fragment," "derivative" and "analog" when referring to the polypeptide of FIG. 1B, mean a polypeptide which retains essentially the same biological function or activity as such polypeptide, i.e. functions as a myotrophin protein, or retains the ability to bind the ligand or the binding molecules even though the polypeptide does not function as a myotrophin protein. Thus, an analog includes, for example, a proprotein which can be activated by cleavage of the proprotein portion to produce an active mature polypeptide. In a preferred embodiment, the polypeptide of the present invention is a recombinant polypeptide.

The fragment, derivative or analog of the polypeptide of FIG. 1B may be (i) one in which one or more of the amino acid residues are substituted with a conserved or non-conserved amino acid residue (preferably a conserved amino acid residue) and such substituted amino acid residue may or may not be one encoded by the genetic code; (ii) one in which one or more of the amino acid residues includes a substituent group; (iii) one in which the mature polypeptide is fused with another compound, such as a compound to increase the half-life of the polypeptide (for example, polyethylene glycol); or (iv) one in which the additional amino acids are fused to the mature polypeptide, such as a leader or secretory sequence or a sequence which is employed for purification of the mature polypeptide or a proprotein sequence. Such fragments, derivatives and analogs are deemed to be within the scope of those skilled in the art from the teachings herein.

Among the particularly preferred embodiments of the invention in this regard are polypeptides having the amino acid sequence of SEQ ID NO:2 set out in FIG. 1B, variants, analogs, derivatives and fragments thereof, and variants, analogs and derivatives of the fragments. Further particularly preferred embodiments of the invention in this regard are polypeptides which retain the activity/function of human myotrophin.

Among preferred variants are those that vary from the polypeptide encoded by HSABH01 by conservative amino acid substitutions. Such substitutions are those that substitute a given amino acid in a polypeptide by another amino acid of like characteristics. Typically seen as conservative substitutions are the replacements, one for another, among the aliphatic amino acids Ala, Val, Leu and ile; interchange of the hydroxyl residues Ser and Thr, exchange of the acidic residues Asp and Glu, substitution between the amide residues Asn and Gln, exchange of the basic residues Lys and Arg and replacements among the aromatic residues Phe and Tyr.

Further particularly preferred in this regard are variants, analogs, derivatives and fragments, and variants, analogs and derivatives of the fragments, having the amino acid sequence of SEQ ID NO:2 of FIG. 1B, in which several, a few, 5 to 10, 1 to 5, 1 to 3, 2, 1 or no amino acid residues are substituted, deleted or added, in any combination. Especially preferred among these are silent substitutions, additions and deletions, which do not alter the properties and activities of human myotrophin. Also especially preferred in this regard are conservative substitutions. Most highly preferred are polypeptides having the amino acid sequence of FIG. 1B without substitutions.

The polypeptides and polynucleotides of the present invention are preferably provided in an isolated form, and preferably are purified to homogeneity.

Fragments or portions of the polypeptides of the present invention may be employed for producing the corresponding full-length polypeptide by peptide synthesis; therefore, the fragments may be employed as intermediates for producing the full-length polypeptides. Fragments or portions of the polynucleotides of the present invention may be used to synthesize full-length polynucleotides of the present invention. Fragments may be "free-standing," i.e., not part of or fused to other amino acids or polypeptides, or they may be comprised within a larger polypeptide of which they form a part or region. When comprised within a larger polypeptide, the presently discussed fragments most preferably form a single continuous region. However, several fragments may be comprised within a single larger polypeptide. For instance, certain preferred embodiments relate to a fragment of a polypeptide encoded by HSABH01 of the present invention comprised within a precursor polypeptide designed for expression in a host and having heterologous pre- and pro-polypeptide regions fused to the amino terminus of the HSABH01 encoded fragment and an additional region fused to the carboxyl terminus of the fragment. Therefore, fragments in one aspect of the meaning intended herein, refers to the portion or portions of a fusion polypeptide or fusion protein encoded by HSABH01.

As representative examples of polypeptide fragments of the invention, there may be mentioned those which have from about 5–15, 10–20, 15–40, 30–55, 41–75, 41–80, 41–90, 50–100, 75–100, 90–115, 100–125, and 110–113 amino acids in length.

In this context "about" includes the particularly recited range and ranges larger or smaller by several, a few, 5, 4, 3, 2 or 1 amino acid residues at either extreme or at both extremes. For instance, about 40–90 amino acids in this context means a polypeptide fragment of 40 plus or minus several, a few, 5, 4, 3, 2 or 1 amino acid residues to 90 plus or minus several a few, 5, 4, 3, 2 or 1 amino acid residues, i.e., ranges as broad as 40 minus several amino acids to 90 plus several amino acids to as narrow as 40 plus several amino acids to 90 minus several amino acids. Highly preferred in this regard are the recited ranges plus or minus as many as 5 amino acids at either or at both extremes. Particularly highly preferred are the recited ranges plus or minus as many as 3 amino acids at either or at both the recited extremes. Especially particularly highly preferred are ranges plus or minus 1 amino acid at either or at both extremes or the recited ranges with no additions or deletions. Most highly preferred of all in this regard are fragments from about 5–15, 10–20, 15–40, 30–55, 41–75, 41–80, 41–90, 50–100, 75–100, 90–115, 100–125, and 110–113 amino acids long.

Among especially preferred fragments of the invention are truncation mutants of human myotrophin. Truncation mutants include polypeptides encoded by HSABH01 having the amino acid sequence of FIG. 1B, or of variants or derivatives thereof, except for deletion of a continuous series of residues (that is, a continuous region, part or portion) that includes the amino terminus, or a continuous series of residues that includes the carboxyl terminus or, as in double truncation mutants, deletion of two continuous series of residues, one including the amino terminus and one including the carboxyl terminus.

Also preferred in this aspect of the invention are fragments characterized by structural or functional attributes of human myotrophin. Preferred embodiments of the invention in this regard include fragments that comprise ankyrin repeats homologous to IκB/rel ankyrin.

Further preferred regions are those that mediate activities of human myotrophin. Most highly preferred in this regard are fragments that have a chemical, biological or other activity of human myotrophin, including those with a similar activity or an improved activity, or with a decreased undesirable activity. Highly preferred in this regard are fragments that contain regions that are homologs in sequence, or in position, or in both sequence and to active regions of related polypeptides, such as IκBα/rel and other inhibitors of NF-KB.

It will be appreciated that the invention also relates to, among others, polynucleotides encoding the aforementioned fragments, polynucleotides that hybridize to polynucleotides encoding the fragments, particularly those that hybridize under stringent conditions, and polynucleotides, such as PCR primers, for amplifying polynucleotides that encode the fragments. In these regards, preferred polynucleotides are those that correspond to the preferred fragments, as discussed above.

Vectors, host cells, expression

The present invention also relates to vectors which contain polynucleotides of the present invention, host cells which are genetically engineered with vectors of the invention and the production of polypeptides of the invention by recombinant techniques.

Host cells can be genetically engineered to incorporate polynucleotides and express polypeptides of the present invention. For instance, polynucleotides may be introduced into host cells using well known techniques of infection, transduction, transfection, transvection and transformation. The polynucleotides may be introduced alone or with other polynucleotides. Such other polynucleotides may be introduced independently, co-introduced or introduced joined to the polynucleotides of the invention.

Thus, for instance, polynucleotides of the invention may be transfected into host cells with another, separate polynucleotide encoding a selectable marker, using standard techniques for co-transfection and selection in, for instance, mammalian cells. In this case the polynucleotides generally will be stably incorporated into the host cell genome.

Alternatively, the polynucleotides may be joined to a vector containing a selectable marker for propagation in a host. The vector construct may be introduced into host cells by the aforementioned techniques. Generally, a plasmid vector is introduced as DNA in a precipitate, such as a calcium phosphate precipitate, or in a complex with a charged lipid. Electroporation may also be used to introduce polynucleotides into a host. If the vector is a virus, it may be packaged in vitro or introduced into a packaging cell and the packaged virus may be transduced into cells. A wide variety of techniques suitable for making polynucleotides and for introducing polynucleotides into cells in accordance with this aspect of the invention are well known and routine to those of skill in the art. Such techniques are reviewed at length in Sambrook et al. which is illustrative of the many laboratory manuals that detail these techniques.

In accordance with this aspect of the invention the vector may be, for example, a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors may also be and preferably are introduced into cells as packaged or encapsidated virus by well known techniques for infection and transduction. Viral vectors may be replication competent or replication defective. In the latter case, viral propagation generally will occur only in complementing host cells.

Preferred among vectors, in certain respects, are those for expression of polynucleotides and polypeptides of the present invention. Generally, such vectors comprise cis-acting control regions effective for expression in a host operatively linked to the polynucleotide to be expressed. Appropriate trans-acting factors are either supplied by the host, supplied by a complementing vector or supplied by the vector itself upon introduction into the host.

In certain preferred embodiments in this regard, the vectors provide for specific expression. Such specific expression may be inducible expression or expression only in certain types of cells or both inducible and cell-specific expression. Particularly preferred among inducible vectors are vectors that can be induced for expression by environmental factors that are easy to manipulate, such as temperature and nutrient additives. A variety of vectors suitable to this aspect of the invention, including constitutive and inducible expression vectors for use in prokaryotic and eukaryotic hosts, are well known and employed routinely by those of skill in the art.

The engineered host cells can be cultured in conventional nutrient media, which may be modified as appropriate for, inter alia, activating promoters, selecting transformants or amplifying genes. Culture conditions, such as temperature, pH and the like, previously used with the host cell selected for expression, generally will be suitable for expression of polypeptides of the present invention as will be apparent to those of skill in the art.

A great variety of expression vectors can be used to express a polypeptide of the invention. Such vectors include chromosomal, episomal and virus-derived vectors e.g., vectors derived from bacterial plasmids, bacteriophages, yeast episomes, yeast chromosomal elements, and viruses such as baculoviruses, papova viruses, SV40, vaccinia viruses, adenoviruses, fowl pox viruses, pseudorabies viruses and retroviruses, and vectors derived from combinations thereof, such as those derived from plasmid and bacteriophage genetic elements, cosmids and phagemids. Generally, any vector suitable to maintain, propagate or express polynucleotides to produce a polypeptide in a host may be used for expression in this regard.

The appropriate DNA sequence may be inserted into the vector by any of a variety of well-known and routine techniques. In general, a DNA sequence for expression is joined to an expression vector by cleaving the DNA sequence and the expression vector with one or more restriction endonucleases and then joining the restriction fragments together using T4 DNA ligase. Procedures for restriction and ligation that can be used to this end are well known and routine to those of skill. Suitable procedures in this regard, and for constructing expression vectors using alternative techniques, which also are well known and routine to those skilled in the art, are set forth in great detail in Sambrook et al.

The DNA sequence in the expression vector is operatively linked to appropriate expression control sequence(s), including, for instance, a promoter to direct mRNA transcription. Representatives of such promoters include the phage lambda PL promoter, the *E. coli* lac, trp and tac promoters, the SV40 early and late promoters and promoters of retroviral LTRs, to name just a few of the well-known promoters. It will be understood that numerous other promoters useful in this aspect of the invention are well known and may be routinely employed by those of skill in the manner illustrated by the discussion and the examples herein.

In general, expression constructs will contain sites for transcription initiation and termination, and, in the transcribed region, a ribosome binding site for translation. The coding portion of the mature transcripts expressed by the constructs will include a translation initiating AUG at the beginning and a termination codon appropriately positioned at the end of the polypeptide to be translated.

In addition, the constructs may contain control regions that regulate as well as engender expression. Generally, in accordance with many commonly practiced procedures, such regions will operate by controlling transcription. Examples include repressor binding sites and enhancers, among others.

Vectors for propagation and expression generally will include selectable markers. Selectable marker genes provide a phenotypic trait for selection of transformed host cells. Preferred markers include, but are not limited to, dihydrofolate reductase or neomycin resistance for eukaryotic cell culture, and tetracycline or ampicillin resistance genes for culturing E. coli and other bacteria. Such markers may also be suitable for amplification. Alternatively, the vectors may contain additional markers for this purpose.

The vector containing the appropriate DNA sequence as described elsewhere herein, as well as an appropriate promoter, and other appropriate control sequences, may be introduced into an appropriate host using a variety of well known techniques suitable for expression therein of a desired polypeptide. Representative examples of appropriate hosts include bacterial cells, such as E. coli, Streptomyces and Salmonella typhimurium cells; fungal cells, such as yeast cells; insect cells such as Drosophila S2 and Spodoptera Sf9 cells; animal cells such as CHO, COS and Bowes melanoma cells; and plant cells. Hosts of a great variety of expression constructs are well known, and those of skill will be enabled by the present disclosure to routinely select a host for expressing a polypeptide in accordance with this aspect of the present invention.

More particularly, the present invention also includes recombinant constructs, such as expression constructs, comprising one or more of the sequences described above. The constructs comprise a vector, such as a plasmid or viral vector, into which such a sequence of the invention has been inserted. The sequence may be inserted in a forward or reverse orientation. In certain preferred embodiments in this regard, the construct further comprises regulatory sequences, including, for example, a promoter, operably linked to the sequence. Large numbers of suitable vectors and promoters are known to those of skill in the art, and there are many commercially available vectors suitable for use in the present invention.

The following vectors, which are commercially available, are provided by way of example. Among vectors preferred for use in bacteria are pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. These vectors are listed solely by way of illustration of the many commercially available and well known vectors that are available to those of skill in the art for use in accordance with this aspect of the present invention. It will be appreciated that any other plasmid or vector suitable for, for example, introduction, maintenance, propagation or expression of a polynucleotide or polypeptide of the invention in a host may be used in this aspect of the invention.

Promoter regions can be selected from any desired gene using vectors that contain a reporter transcription unit lacking a promoter region, such as a chloramphenicol acetyl transferase ("CAT") transcription unit, downstream of a restriction site or sites for introducing a candidate promoter fragment; i.e., a fragment that may contain a promoter. As is well known, introduction into the vector of a promoter-containing fragment at the restriction site upstream of the CAT gene engenders production of CAT activity, which can be detected by standard CAT assays. Vectors suitable to this end are well known and readily available. Two examples of such vectors include pKK232-8 and pCM7. Thus, promoters for expression of polynucleotides of the present invention include not only well known and readily available promoters, but also promoters that may be readily obtained by the foregoing technique, using a reporter gene.

Among known bacterial promoters suitable for expression of polynucleotides and polypeptides in accordance with the present invention are the E. coli lacI and lacZ promoters, the T3 and T7 promoters, the gpt promoter, the lambda PR, PL promoters and the trp promoter.

Among known eukaryotic promoters suitable in this regard are the CMV immediate early promoter, the HSV thymidine kinase promoter, the early and late SV40 promoters, the promoters of retroviral LTRs, such as those of the Rous Sarcoma Virus("RSV"), and metallothionein promoters, such as the mouse metallothionein-I promoter.

Selection of appropriate vectors and promoters for expression in a host cell is a well known procedure and the requisite techniques for construction of expression vectors, introduction of the vector into the host and expression in the host are routine skills in the art.

The present invention also relates to host cells containing the above-described constructs. The host cell can be a higher eukaryotic cell, such as a mammalian cell, a lower eukaryotic cell, such as a yeast cell, or a prokaryotic cell, such as a bacterial cell.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals.

Constructs in host cells can be used in a conventional manner to produce the gene product encoded by the recombinant sequence. Alternatively, the polypeptides of the invention can be synthetically produced by conventional peptide synthesizers.

Mature proteins can be expressed in mammalian cells, yeast, bacteria, or other cells under the control of appropriate promoters. Cell-free translation systems can also be employed to produce such proteins using RNAs derived from the DNA constructs of the present invention. Appropriate cloning and expression vectors for use with prokaryotic and eukaryotic hosts are described by Sambrook et al.

Generally, recombinant expression vectors will include origins of replication, a promoter derived from a highly-expressed gene to direct transcription of a downstream structural sequence, and a selectable marker to permit isolation of vector containing cells following exposure to the vector. Among suitable promoters are those derived from the genes that encode glycolytic enzymes such as 3-phosphoglycerate kinase ("PGK"), a-factor, acid phosphatase, and heat shock proteins, among others. Selectable markers include the ampicillin resistance gene of E. coli and the trp1 gene of S. cerevisiae.

Transcription of DNA encoding the polypeptides of the present invention by higher eukaryotes may be increased by inserting an enhancer sequence into the vector. Enhancers are cis-acting elements of DNA, usually from about 10 to 300 bp, that act to increase transcriptional activity of a promoter in a given host cell-type. Examples of enhancers include the SV40 enhancer, which is located on the late side of the replication origin at bp 100 to 270, the cytomegalovirus early promoter enhancer, the polyoma enhancer on the late side of the replication origin, and adenovirus enhancers.

A polynucleotide of the invention encoding the heterologous structural sequence of a polypeptide of the invention generally will be inserted into the vector using standard techniques so that it is operably linked to the promoter for expression. The polynucleotide will be positioned so that the transcription start site is located appropriately 5' to a ribosome binding site. The ribosome binding site will be 5' to the AUG that initiates translation of the polypeptide to be expressed. Generally, there will be no other open reading frames that begin with an initiation codon, usually AUG, and lie between the ribosome binding site and the initiation codon. Also, generally, there will be a translation stop codon at the end of the polypeptide and a polyadenylation signal and transcription termination signal appropriately disposed at the 3' end of the transcribed region.

Appropriate secretion signals may be incorporated into the expressed polypeptide for secretion of the translated protein into the lumen of the endoplasmic reticulum, the periplasmic space or the extracellular environment. The signals may be endogenous to the polypeptide or heterologous.

The polypeptide may be expressed in a modified form, such as a fusion protein, and may include not only secretion signals but also additional heterologous functional regions. Thus, for example, a region of additional amino acids, particularly charged amino acids, may be added to the N-terminus of the polypeptide to improve stability and persistence in the host cell during purification or subsequent handling and storage. A region may also be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Suitable prokaryotic hosts for propagation, maintenance or expression of polynucleotides and polypeptides in accordance with the invention include *Escherichia coli, Bacillus subtilis* and *Salmonella typhimurium*. Various species of Pseudomonas, Streptomyces, and Staphylococcus are also suitable hosts in this regard. Moreover, many other hosts also known to those of skill may be employed in this regard.

As a representative but non-limiting example, useful expression vectors for bacterial use can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and GEM1 (Promega Biotec, Madison, Wis., USA). In these vectors, the pBR322 "backbone" sections are combined with an appropriate promoter and the structural sequence to be expressed.

Following transformation of a suitable host strain, the host strain is grown to an appropriate cell density. Where the selected promoter is inducible, it is induced by appropriate means (e.g., temperature shift or exposure to chemical inducer) and cells are cultured for an additional period. Cells typically then are harvested by centrifugation, disrupted by physical or chemical means, and the resulting crude extract retained for further purification.

Microbial cells employed in expression of proteins can be disrupted by any convenient method, including freeze-thaw cycling, sonication, mechanical disruption, or use of cell lysing agents. Such methods are well known to those skilled in the art.

Various mammalian cell culture systems can be employed for expression, as well. Examples of mammalian expression systems include the C127, 3T3, CHO, HeLa, human kidney 293 and BHK cell lines and the COS-7 line of monkey kidney fibroblasts, described by Gluzman et al., *Cell,* 1981, 23:175.

Mammalian expression vectors will comprise an origin of replication, a suitable promoter and enhancer, and any necessary ribosome binding sites, polyadenylation sites, splice donor and acceptor sites, transcriptional termination sequences, and 5' flanking non-transcribed sequences that are necessary for expression. In certain preferred embodiments, DNA sequences derived from the SV40 splice sites and the SV40 polyadenylation sites are used for required non-transcribed genetic elements.

Polypeptides encoded by HSABH01 can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification. Well known techniques for refolding proteins may be employed to regenerate active conformation when the polypeptide is denatured during isolation and or purification.

Polypeptides of the present invention can be produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or non-glycosylated. In addition, polypeptides of the invention may include an initial modified methionine residue, in some cases as a result of host-mediated processes.

Human myotrophin polynucleotides such as HSABH01 and polypeptides encoded thereby may be used in accordance with the present invention for a variety of applications, particularly those that make use of the chemical and biological properties of human myotrophin. Additional applications relate to diagnosis and to treatment of disorders of cells, tissues and organisms. These aspects of the invention are illustrated further by the following discussion.

Polynucleotide assays

This invention is also related to the use of human myotrophin polynucleotides to detect complementary polynucleotides for use, for example, as a diagnostic reagent. Detection of human myotrophin associated with a dysfunction will provide a diagnostic tool that can add to or define diagnosis of a disease or susceptibility to a disease. The human myotrophin gene, or mutants of this gene, may be detected at the DNA level by a variety of techniques. Nucleic acids for diagnosis may be obtained from a patient's cells, such as from blood, urine, saliva, tissue biopsy or autopsy material. The genomic DNA may be used directly for detection or may be amplified enzymatically by using PCR prior to analysis. PCR (Saiki et al., *Nature,* 1986, 324:163–166). RNA or cDNA may also be used in similar fashion. As an example, PCR primers complementary to a portion of the HSABH01 nucleic acid sequence can be used to identify and analyze expression and mutations of human myotrophin. For example, deletions and insertions can be detected by a change in size of the amplified product in comparison to the normal genotype. Point mutations can be identified by hybridizing amplified DNA to radiolabeled HSABH01 RNA or, radiolabeled HSABH01 antisense DNA sequences. Perfectly matched sequences can be distinguished from mismatched duplexes by RNase A digestion or by differences in melting temperatures.

Sequence differences between a reference gene and genes having mutations may also be revealed by direct DNA sequencing. In addition, cloned DNA segments may be employed as probes to detect specific DNA segments. The sensitivity of such methods can be greatly enhanced by appropriate use of PCR or other amplification methods. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alterations in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science,* 1985, 230:1242).

Sequence changes at specific locations may also be revealed by nuclease protection assays, such as RNase and S1 protection or the chemical cleavage method (e.g., Cotton et al., *Proc. Natl. Acad. Sci., USA,* 1985, 85: 4397–4401).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In accordance with a further aspect of the invention, there is provided a process for diagnosing or determining a susceptibility to diseases or disorders relating to cellular hypertrophy, such as diabetic nephropathy and hypertension-induced nephropathy, benign prostatic hypertrophy, restenosis, atherosclerosis, aneurysms and strokes, and in particular, diseases relating to cardiac hypertrophy, such as congestive heart failure, dilated cardiomyopathy, and hypertension, among others. Detection of the human myotrophin gene may be indicative of a susceptibility to diseases or disorders relating to cellular hypertrophy, such as diabetic nephropathy and hypertension-induced nephropathy, benign prostatic hypertrophy, restenosis, atherosclerosis, aneurysms and strokes and in particular, diseases relating to cardiac hypertrophy, such as congestive heart failure, dilated cardiomyopathy, and hypertension, among others; the nucleic acid sequences described above may be employed in an assay for ascertaining such susceptibility.

The invention provides a process for diagnosing diseases or disorder, particularly, those relating to cellular hypertrophy such as diabetic nephropathy and hypertension-induced nephropathy, benign prostatic hypertrophy, restenosis, atherosclerosis, aneurysms, and strokes and disease relating to cardiac hypertrophy, such as congestive heart failure, dilated cardiomyopathy, and hypertension, among others; comprising determining from a sample derived from a patient an abnormally decreased or increased level of expression of polynucleotide having the sequence of FIG. 1A, SEQ ID NO: 1. Decreased or increased expression of polynucleotide can be measured using any of the methods well known in the art for the quantitation of polynucleotides, such as, for example, PCR, RT-PCR, RNase protection, Northern blotting and other hybridization methods.

In addition to more conventional gel-electrophoresis and DNA sequencing, mutations can also be detected by in situ analysis.

Chromosome assays

The sequences of the present invention are also valuable for chromosome identification. The sequence is specifically targeted to and can hybridize with a particular location on an individual human chromosome. Moreover, there is a current need for identifying particular sites on the chromosome. Few chromosome marking reagents based on actual sequence data (repeat polymorphisms) are presently available for marking chromosomal location. The mapping of DNAs to chromosomes according to the present invention is an important first step in correlating those sequences with gene associated disease.

Briefly, sequences can be mapped to chromosomes by preparing PCR primers (preferably 15–25 bp) from the cDNA. Computer analysis of the 3' untranslated region is used to rapidly select primers that do not span more than one exon in the genomic DNA, because primers that span more than one exon could complicate the amplification process. These primers are then used for PCR screening of somatic cell hybrids containing individual human chromosomes. Only those hybrids containing the human gene corresponding to the primer will yield an amplified fragment.

PCR mapping of somatic cell hybrids is a rapid procedure for assigning a particular DNA to a particular chromosome. Using the present invention with the same oligonucleotide primers, sublocalization can be achieved with panels of fragments from specific chromosomes or pools of large genomic clones in an analogous manner. Other mapping strategies that can be used similarly to map to the chromosome include in situ hybridization, prescreening with labeled flow-sorted chromosomes and preselection by hybridization to construct chromosome specific-cDNA libraries.

Fluorescence in situ hybridization (FISH) of a cDNA clone to a metaphase chromosomal spread can be used to provide a precise chromosomal location in one step. This technique can be used with cDNAs as short as 50 to 60 bases. For a review of this technique, see Verma et al., HUMAN CHROMOSOMES: A MANUAL OF BASIC TECHNIQUES, PERGAMON PRESS, NEW YORK, 1988.

As an example of how this technique is performed, human myotrophin DNA is digested and purified with QIAEX II DNA purification kit (Qiagen, Inc., Chatsworth, Calif.) and ligated to Super Cos1 cosmid vector (Stratagene, La Jolla, Calif.). DNA is purified using Qiagen Plasmid Purification Kit (Qiagen, Inc., Chatsworth, Calif.) and 1 mg is labeled by nick translation in the presence of Biotin-dATP using BioNick Labeling Kit (GibcoBRL, Life Technologies Inc., Gaithersburg, Md.). Biotinylation is detected with GENE-TECT Detection System (Clontech Laboratories, Inc. Palo Alto, Calif.). In situ hybridization is performed on slides using ONCOR Light Hybridization Kit (Oncor, Gaithersburg, Md.) to detect single copy sequences on metaphase chromosomes. Peripheral blood of normal donors is cultured for three days in RPMI 1640 supplemented with 20% FCS, 3% PHA and penicillin/streptomycin, synchronized with $10^{-7}$ M methotrexate for 17 hours, and washed twice with unsupplemented RPMI. Cells are then incubated with $10^{-3}$ M thymidine for 7 hours. The cells are arrested in metaphase after a 20 minute incubation with colcemid (0.5 µg/ml) followed by hypotonic lysis in 75 mM KCl for 15 minutes at 37° C. Cell pellets are then spun out and fixed in Carnoy's fixative (3:1 methanol/acetic acid).

Metaphase spreads are prepared by adding a drop of the suspension onto slides and air drying the suspension. Hybridization is performed by adding 100 ng of probe suspended in 10 ml of hybridization mix (50% formamide, 2× SSC, 1% dextran sulfate) with blocking human placental DNA (1 µg/ml). Probe mixture is denatured for 10 minutes in a 70° C. water bath and incubated for 1 hour at 37° C., before placement on a prewarmed (37° C.) slide, previously denatured in 70% formamide/2× SSC at 70° C., dehydrated in ethanol series, and chilled to 4° C.

Slides are incubated for 16 hours at 37° C. in a humidified chamber. Slides are washed in 50% formamide/2× SSC for 10 minutes at 41° C. and 2× SSC for 7 minutes at 37° C. Hybridization probe is detected by incubation of the slides with FTC-Avidin (Oncor, Gaithersburg, Md.), according to the manufacturer's protocol. Chromosomes are counterstained with propridium iodine suspended in mounting medium. Slides are visualized using a Leitz ORTHOPLAN 2-epifluorescence microscope and five computer images are taken using a Imagenetics Computer and Macintosh printer.

Once a sequence has been mapped to a precise chromosomal location, the physical position of the sequence on the chromosome can be correlated with genetic map data. Such data are found, for example, in V. McKusick, Mendelian Inheritance in Man (available on line through Johns Hopkins University Welch Medical Library). The relationship between genes and diseases that have been mapped to the same chromosomal region are then identified through linkage analysis (coinheritance of physically adjacent genes).

It is then necessary to determine the differences in the cDNA or genomic sequence between affected and unaffected individuals. If a mutation is observed in some or all of the affected individuals but not in any normal individuals, then the mutation is likely to be the causative agent of the disease.

With current resolution of physical mapping and genetic mapping techniques, a cDNA precisely localized to a chromosomal region associated with the disease could be one of between 50 and 500 potential causative genes assuming 1 megabase mapping resolution and one gene per 20 kb.

Polypeptide assays

The present invention also relates to diagnostic assays for detecting levels of human myotrophin protein in cells and tissues. Such assays may be quantitative or qualitative. Thus, for instance, a diagnostic assay in accordance with the invention for detecting over-expression of human myotrophin protein compared to normal control tissue samples may be used to detect the presence of a disease/disorder relating to cellular hypertrophy such as diabetic nephropathy and hypertension-induced nephropathy, benign prostatic hypertrophy, restenosis, atherosclerosis, aneurysms, and strokes and in particular, disease relating to cardiac hypertrophy, such as congestive heart failure, dilated cardiomyopathy, and hypertension, among others. Assay techniques that can be used to determine levels of a protein, such as an human myotrophin protein of the present invention, in a sample derived from a host are well-known to those of skill in the art. Such assay methods include radioimmunoassays, competitive-binding assays, Western Blot analysis and enzyme linked immunosorbent assays (ELISAs). Among these, ELISAs are frequently preferred. An ELISA assay initially comprises preparing an antibody specific to human myotrophin, preferably a monoclonal antibody. In addition a reporter antibody generally is prepared which binds to the monoclonal antibody. The reporter antibody is attached to a detectable reagent such as a radioactive, fluorescent or enzymatic reagent, in this example, horseradish peroxidase enzyme.

To carry out an ELISA, a sample is removed from a host and incubated on a solid support, e.g. a polystyrene dish, that binds the proteins in the sample. Any free protein binding sites on the dish are then covered by incubating with a non-specific protein such as bovine serum albumin. The monoclonal antibody is then incubated in the dish during which time the monoclonal antibodies attach to any myotrophin proteins attached to the polystyrene dish. Unbound monoclonal antibody is washed out with buffer. The reporter antibody linked to horseradish peroxidase is placed in the dish resulting in binding of the reporter antibody to any monoclonal antibody bound to the human myotrophin protein. Unattached reporter antibody is then washed out. Reagents for peroxidase activity, including a calorimetric substrate are then added to the dish. Immobilized peroxidase, linked to human myotrophin through the primary and secondary antibodies, produces a colored reaction product. The amount of color developed in a given time period indicates the amount of human myotrophin protein present in the sample. Quantitative results typically are obtained by reference to a standard curve.

A competition assay may also be employed wherein antibodies specific to human myotrophin are attached to a solid support and labeled human myotrophin encoded by HSABH01 and a sample derived from the host are passed over the solid support. The amount of detected label attached to the solid support can be correlated to a quantity of human myotrophin in the sample.

Antibodies

Polypeptides encoded by HSABH01, their fragments or other derivatives, or analogs thereof, or cells expressing them can also be used as immunogens to produce antibodies thereto. These antibodies can be, for example, polyclonal or monoclonal antibodies. The present invention also includes chimeric, single chain, and humanized antibodies, as well as Fab fragments, or the product of an Fab expression library. Various procedures known in the art may be used for the production of such antibodies and fragments.

Antibodies generated against polypeptides encoded by HSABH01 of the present invention can be obtained by direct injection of the polypeptides into an animal, preferably a nonhuman. The antibody so obtained will then bind the polypeptide itself. In this manner, even a sequence encoding only a fragment of the polypeptide can be used to generate antibodies binding the whole native polypeptide. Such antibodies can then be used to isolate the polypeptide from tissue expressing that polypeptide.

For preparation of monoclonal antibodies, any technique which provides antibodies produced by continuous cell line cultures can be used. Examples include the hybridoma technique (Kohler, G. and Milstein, C., *Nature*, 1975, 256:495–497), the trioma technique, the human B-cell hybridoma technique (Kozbor et al., *Immunology Today*, 1983, 4:72) and the EBV-hybridoma technique (Cole et al., MONOCLONAL ANTIBODIES AND CANCER THERAPY, pages 77–96, Alan R. Liss, Inc., 1985).

Techniques described for the production of single chain antibodies (U.S. Pat. No. 4,946,778) can also be adapted to produce single chain antibodies to immunogenic polypeptide products of this invention. Also, transgenic mice, or other organisms including other mammals, may be used to express humanized antibodies to immunogenic polypeptide products of this invention.

The above-described antibodies may be employed to isolate or to identify clones expressing the polypeptide or purify the polypeptide of the present invention by attachment of the antibody to a solid support for isolation and/or purification by affinity chromatography.

Antibodies against polypeptide encoded by HSABH01 or fragments thereof may also be employed to inhibit disease relating to cellular hypertrophy such as diabetic nephropathy and hypertension-induced nephropathy, benign prostatic hypertrophy, restenosis, atherosclerosis, aneurysms, and strokes and in particular, disease relating to cardiac hypertrophy, such as congestive heart failure, dilated cardiomyopathy, and hypertension, among others.

Human myotrophin binding molecules and assays

Polypeptides encoded by HSABH01 can be used to isolate proteins which interact with it; this interaction can be a target for interference. Inhibitors of protein—protein interactions between polypeptides encoded by HSABH01 and other factors could lead to the development of pharmaceutical agents for the modulation of human myotrophin activity.

Thus, this invention also provides a method for identification of binding molecules to human myotrophin. Genes encoding proteins for binding molecules to human myotrophin can be identified by numerous methods known to those of skill in the art, for example, ligand panning and FACS sorting. Such methods are described in many laboratory manuals such as, for instance, Coligan et al., CURRENT PROTOCOLS IN IMMUNOLOGY 1, Chapter 5, 1991.

For example, the yeast two-hybrid system provides methods for detecting the interaction between a first test protein and a second test protein, in vivo, using reconstitution of the activity of a transcriptional activator. The method is disclosed in U.S. Pat. No. 5,283,173; reagents are available from Clontech and Stratagene. Briefly, HSABH01 cDNA is fused to a Gal4 transcription factor DNA binding domain and expressed in yeast cells. cDNA library members obtained from cells of interest are fused to a transactivation domain of Gal4. cDNA clones which express proteins which can interact with human myotrophin will lead to reconstitution of Gal4 activity and transactivation of expression of a reporter gene such as Gal4-lacZ.

An alternative method involves screening of λgt11, λZAP (Stratagene) or equivalent cDNA expression libraries with recombinant polypeptides encoded by HSABH01. Recombinant proteins or fragments thereof are fused to small peptide tags such as FLAG, HSV or GST. The peptide tags can possess convenient phosphorylation sites for a kinase such as heart muscle creatine kinase or they can be biotinylated. Recombinant HSABH01 encoded polypeptides can be phosphorylated with $^{32}[p]$ or used unlabeled and detected with streptavidin or antibodies against the tags. λgt11cDNA expression libraries are made from cells of interest and are incubated with the recombinant HSABH01 encoded polypeptides, washed and cDNA clones which interact with these polypeptides isolated. Such methods are routinely used by skilled artisans. See, e.g., Sambrook et al.

Another method is the screening of a mammalian expression library. In this method, cDNAs are cloned into a vector between a mammalian promoter and polyadenylation site and transiently transfected in COS or 293 cells. Forty-eight hours later, the binding protein is detected by incubation of fixed and washed cells with labeled human myotrophin encoded by HSABH01. In a preferred embodiment, the human myotrophin is iodinated, and any bound myotrophin is detected by autoradiography. See Sims et al., Science, 1988, 241:585–589 and McMahan et al., EMBO J, 1991, 10:2821–2832. In this manner, pools of cDNAs containing the cDNA encoding the binding protein of interest can be selected and the cDNA of interest can be isolated by further subdivision of each pool followed by cycles of transient transfection, binding and autoradiography. Alternatively, the cDNA of interest can be isolated by transfecting the entire cDNA library into mammalian cells and panning the cells on a dish containing human myotrophin bound to the plate. Cells which attach after washing are lysed and the plasmid DNA isolated, amplified in bacteria, and the cycle of transfection and panning repeated until a single cDNA clone is obtained. See Seed et al, Proc. Natl. Acad. Sci. USA, 1987, 84:3365 and Aruffo et al., EMBO J., 1987, 6:3313. If the binding protein is secreted, its cDNA can be obtained by a similar pooling strategy once a binding or neutralizing assay has been established for assaying supernatants from transiently transfected cells. General methods for screening supernatants are disclosed in Wong et al., Science, 1985, 228:810–815.

Another method involves isolation of proteins interacting with human myotrophin directly from cells. Fusion proteins of human myotrophin with GST or small peptide tags are made and immobilized on beads. Biosynthetically labeled or unlabeled protein extracts from the cells of interest are prepared, incubated with the beads and washed with buffer. Proteins interacting with human myotrophin are eluted specifically from the beads and analyzed by SDS-PAGE. Binding partner primary amino acid sequence data are obtained by microsequencing. Optionally, the cells can be treated with agents that induce a functional response such as tyrosine phosphorylation of cellular proteins. An example of such an agent would be a growth factor or cytokine such as interleukin-2.

Another method is immunoaffinity purification. Recombinant myotrophin encoded by HSABH01 is incubated with labeled or unlabeled cell extracts and immunoprecipitated with anti-myotrophin antibodies. The immunoprecipitate is recovered with protein A-Sepharose and analyzed by SDS-PAGE. Unlabelled proteins are labeled by biotinylation and detected on SDS gels with streptavidin. Binding partner proteins are analyzed by microsequencing. Further, standard biochemical purification steps known to those skilled in the art may be used prior to microsequencing.

Yet another alternative method involves screening of peptide libraries for binding partners. Recombinant tagged or labeled myotrophin encoded by HSABH01 is used to select peptides from a peptide or phosphopeptide library which interact with human myotrophin. Sequencing of the peptides leads to identification of consensus peptide sequences which might be found in interacting proteins.

Human myotrophin binding partners identified by any of these methods or other methods, which would be known to those of ordinary skill in the art, as well as those putative binding partners discussed above, can be used in the assay method of the invention. Assaying for the presence of myotrophin/binding partner complex is accomplished by, for example, the yeast two-hybrid system, ELISA or immunoassays using antibodies specific for the complex. In the presence of test substances which interrupt or inhibit formation of myotrophin/binding partner interaction, a decreased amount of complex will be determined relative to a control lacking the test substance.

Assays for free human myotrophin or binding partner are accomplished by, for example, ELISA or immunoassay using specific antibodies or by incubation of radiolabeled human myotrophin encoded by HSABH01 with cells or cell membranes followed by centrifugation or filter separation steps. In the presence of test substances which interrupt or inhibit formation of myotrophin/binding partner interaction, an increased amount of free myotrophin or free binding partner will be determined relative to a control lacking the test substance.

Polypeptides of the invention also can be used to assess human myotrophin binding capacity of myotrophin binding molecules in cells or in cell-free preparations.

Agonists and antagonists—assays and molecules

The human myotrophin encoded by HSABH01 of the present invention may be employed in a screening process for compounds which activate (agonists) or inhibit activation (antagonists) of human myotrophin.

In general, such screening procedures involve producing appropriate cells which express a polypeptide encoded by HSABH01. Such cells include cells from mammals, yeast, Drosophila or *E. coli*. In particular, a polynucleotide of the present invention is employed to transfect cells to thereby express the human myotrophin. Cells expressing the receptor are then contacted with a test compound to observe binding, stimulation or inhibition of a functional response.

One such screening procedure involves the use of melanophores which are transfected to express the HSABH01 of the present invention. Such a screening technique is described in PCT WO92/01810 . In one embodiment, this technique is employed to screen for compounds which inhibit activation of a polypeptide of the present invention by contacting the melanophore cells which encode the polypeptide with both a myotrophin ligand and a compound to be screened. Inhibition of the signal generated by the myotrophin ligand indicates that a compound is a potential antagonist for the polypeptide, i.e., inhibits activation of the polypeptide. The technique may also be employed for screening of compounds which activate the polypeptide by contacting such cells with compounds to be screened and determining whether such compound generates a signal, i.e., activates the polypeptide.

Other screening techniques include the use of cells which express the HSABH01 encoded polypeptide (for example, transfected CHO cells) in a system which measures extracellular pH changes caused by activation of polypeptide. (See e.g., *Science,* 1989, 246:181–296). In this technique, compounds may be contacted with cells expressing the polypeptide of the present invention. A second messenger response, e.g., signal transduction or pH change, is then measured to determine whether the potential compound activates or inhibits activity of this protein.

Another screening technique involves introducing HSABH01 RNA encoding human myotrophin into *Xenopus* oocytes to transiently express the protein. The oocytes are then contacted with the myotrophin ligand and a compound to be screened. Inhibition or activation of the myotrophin is then determined by detection of a signal, such as, calcium, proton, or other ions, in the case of screening for compounds which are thought to inhibit activation of this protein.

Another screening technique involves expressing HSABH01 encoded polypeptides in which the polypeptide is linked to phospholipase C or D. Representative examples of such cells include, but are not limited to, endothelial cells, smooth muscle cells, and embryonic kidney cells. The screening may be accomplished as hereinabove described by detecting activation of the protein or inhibition of activation of the protein from the phospholipase second signal.

Another method involves screening for compounds which are antagonists and thus inhibit activation of the polypeptide of the present invention by determining inhibition of binding of labeled ligand to cells which contain the protein. Such a method involves transfecting a eukaryotic cell with HSABH01 DNA encoding human myotrophin such that the cell expresses the protein. The cells are then contacted with a compound in the presence of a labeled form of a known ligand. The ligand can be labeled, e.g., by radioactivity. The amount of labeled ligand bound to the human myotrophin is measured, e.g., by measuring radioactivity associated with transfected cells. If the compound binds to the myotrophin protein, the binding of labeled ligand to the protein is inhibited as determined by a reduction of labeled ligand.

Another method for detecting agonists or antagonists for the receptor of the present invention is the yeast based technology described in U.S. Pat. No. 5,482,835.

The present invention also provides a method for determining whether a ligand not known to be capable of binding to human myotrophin can bind to such protein. This method comprises contacting a mammalian cell which expresses HSABH01 cDNA with the ligand under conditions permitting binding of ligands to the encoded protein, and detecting the presence of a ligand which binds to the protein thereby determining whether the ligand binds to human myotrophin. The systems hereinabove described for determining agonists and/or antagonists may also be employed for determining ligands which bind to the receptor.

Examples of potential human myotrophin antagonists include antibodies or, in some cases, oligonucleotides which bind to the protein but do not elicit a second messenger response such that the activity of the protein is prevented.

A potential antagonist also includes an antisense construct prepared through the use of antisense technology. Antisense technology can be used to control gene expression through triple-helix formation or antisense DNA or RNA, both methods of which are based on binding of a polynucleotide to DNA or RNA. For example, the 5' coding portion of the polynucleotide sequence, which encodes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., *Nucl. Acids Res.,* 1979, 6:3073; Cooney et al., *Science,* 1988, 241:456; and Dervan et al., *Science,* 1991, 251:1360), thereby preventing transcription and production of the protein. The antisense RNA oligonucleotide hybridizes to the mRNA in vivo and blocks translation of the mRNA molecule into the protein (antisense—see Okano, *J. Neurochem., (*1991) 56:560; Oligodeoxynucleotides as Antisense Inhibitors of Gene Expression, CRC Press, Boca Raton, Fla. (1988)). The oligonucleotides described above can also be delivered to cells such that the antisense RNA or DNA is expressed in vivo to inhibit production of human myotrophin.

Myotrophin proteins are ubiquitous in the mammalian host and are responsible for many biological functions, including many pathologies. Accordingly, it is desirous to find compounds and drugs which stimulate myotrophin on the one hand and which can inhibit the function of myotrophin on the other hand.

Agonists for human myotrophin may be employed as research tools in the study of cellular hypertrophy relating to myotrophin activation.

Antagonists for human myotrophin may be employed for a variety of therapeutic and prophylactic purposes for such diseases or disorders relating to cellular hypertrophy such as diabetic nephropathy and hypertension-induced nephropathy, benign prostatic hypertrophy, restenosis, atherosclerosis, aneurysms, and strokes and in particular, disease relating to cardiac hypertrophy, such as congestive heart failure, dilated cardiomyopathy, and hypertension, among others.

This invention additionally provides a method of treating an abnormal condition related to an excess of human myotrophin activity which comprises administering to a subject an inhibitor compound (antagonist) as hereinabove described along with a pharmaceutically acceptable carrier in an amount effective to inhibit activation by blocking binding of ligands to human myotrophin, or by inhibiting a second signal, and thereby alleviating the abnormal condition.

The invention also provides a method of treating abnormal conditions related to an under-expression of human myotrophin and its activity, which comprises administering to a subject a therapeutically effective amount of a compound which activates the polypeptide of the present invention (agonist) as described above, in combination with a pharmaceutically acceptable carrier, to thereby alleviate the abnormal condition.

Compositions and Kits

Polynucleotides such as HSABH01 or polypeptides encoded thereby of the present invention, and compounds which activate or inhibit such polypeptides, may be employed in combination with a suitable pharmaceutical carrier. Such compositions comprise a therapeutically effective amount of the polypeptide or compound, and a pharmaceutically acceptable carrier or excipient. Such carriers include but are not limited to, saline, buffered saline, dextrose, water, glycerol, ethanol, and combinations thereof. The formulation should suit the mode of administration. Selection of an appropriate carrier in accordance with the mode of administration is routinely performed by those skilled in the art.

The invention further relates to pharmaceutical packs and kits comprising one or more containers filled with one or more of the ingredients of the aforementioned compositions of the invention.

Administration

Polypeptides and other compounds of the present invention may be employed alone or in conjunction with other compounds, such as therapeutic compounds.

The pharmaceutical compositions may be administered in any effective, convenient manner including, for instance, administration by topical, oral, anal, vaginal, intravenous, intraperitoneal, intramuscular, subcutaneous, intranasal or intradermal routes, among others.

The pharmaceutical compositions generally are administered in an amount effective for treatment or prophylaxis of a specific indication or indications. In general, the compositions are administered in an amount of at least about 10 $\mu$g/kg body weight. In most cases they will be administered in an amount not in excess of about 8 mg/kg body weight per day. Preferably, in most cases, the administered dose is from about 10 $\mu$g/kg to about 1 mg/kg body weight, daily. It will be appreciated that optimum dosage will be determined by standard methods for each treatment modality and indication, taking into account the indication, its severity, route of administration, complicating conditions and the like.

Gene therapy

The human myotrophin polynucleotides, polypeptides encoded thereby, and agonists and antagonists that are polypeptides may be employed in accordance with the present invention by expression of such polypeptides in treatment modalities often referred to as "gene therapy."

Thus, for example, cells from a patient may be engineered with a polynucleotide, such as a DNA or RNA, to encode a polypeptide ex vivo. The engineered cells can then be provided to a patient to be treated with the polypeptide. In this embodiment, cells may be engineered ex vivo, for example, by the use of a retroviral plasmid vector containing RNA encoding a polypeptide of the present invention. Such methods are well-known in the art and their use in the present invention will be apparent from the teachings herein.

Similarly, cells may be engineered in vivo for expression of a polypeptide in vivo by procedures known in the art. For example, a polynucleotide of the invention may be engineered for expression in a replication defective retroviral vector, as discussed above. The retroviral expression construct may then be isolated and introduced into a packaging cell transduced with a retroviral plasmid vector containing RNA encoding a polypeptide of the present invention such that the packaging cell now produces infectious viral particles containing the gene of interest. These producer cells may be administered to a patient for engineering cells in vivo and expression of the polypeptide in vivo. These and other methods for administering a polypeptide of the present invention should be apparent to those skilled in the art from the teachings of the present invention.

Retroviruses from which the retroviral plasmid vectors herein above mentioned may be derived include, but are not limited to, Moloney Murine Leukemia Virus, Spleen Necrosis Virus, Rous Sarcoma Virus, Harvey Sarcoma Virus, Avian Leukosis Virus, Gibbon Ape Leukemia Virus, Human Immunodeficiency Virus, Adenovirus, Myeloproliferative Sarcoma Virus, and Mammary Tumor Virus. In a preferred embodiment, the retroviral plasmid vector is derived from Moloney Murine Leukemia Virus.

Such vectors will include one or more promoters for expressing the polypeptide. Suitable promoters which may be employed include, but are not limited to, the retroviral LTR; the SV40 promoter; and the human cytomegalovirus (CMV) promoter described in Miller et al., *Biotechniques*, 1989, 7:980–990. Cellular promoters such as eukaryotic cellular promoters including, but not limited to, the histone, RNA polymerase III, and $\beta$-actin promoters can also be used. Additional viral promoters which may be employed include, but are not limited to, adenovirus promoters, thymidine kinase (TK) promoters, and B19 parvovirus promoters. The selection of a suitable promoter will be apparent to those skilled in the art from the teachings contained herein.

The nucleic acid sequence encoding the polypeptide of the present invention will be placed under the control of a suitable promoter. Suitable promoters which may be employed include, but are not limited to, adenoviral promoters, such as the adenoviral major late promoter; or heterologous promoters, such as the cytomegalovirus (CMV) promoter; the respiratory syncytial virus (RSV) promoter; inducible promoters, such as the MMT promoter, the metallothionein promoter; heat shock promoters; the albumin promoter; the ApoAI promoter; human globin promoters; viral thymidine kinase promoters, such as the Herpes Simplex thymidine kinase promoter; retroviral LTRs (including the modified retroviral LTRs herein above described); the $\beta$-actin promoter; and human growth hormone promoters. The promoter may also be the native promoter which controls the gene encoding the polypeptide.

The retroviral plasmid vector is employed to transduce packaging cell lines to form producer cell lines. Examples of packaging cells which may be transfected include, but are not limited to, the PE501, PA317, Y-2, Y-AM, PA12, T19-14X, VT-19-17-H2, YCRE, YCRIP, GP+E-86, GP+envAm12, and DAN cell lines as described in Miller, A., *Human Gene Therapy*, 1990, 1:5–14. The vector may be transduced into the packaging cells through any means known in the art. Such means include, but are not limited to, electroporation, the use of liposomes, and $CaPO_4$ precipitation. In one alternative, the retroviral plasmid vector may be encapsulated into a liposome, or coupled to a lipid, and then administered to a host.

The producer cell line will generate infectious retroviral vector particles, which include the nucleic acid sequence(s) encoding the polypeptides. Such retroviral vector particles may then be employed to transduce eukaryotic cells, either in vitro or in vivo. The transduced eukaryotic cells will express the nucleic acid sequence(s) encoding the polypeptide. Eukaryotic cells which may be transduced include, but are not limited to, embryonic stem cells, embryonic carcinoma cells, as well as hematopoietic stem cells, hepatocytes, fibroblasts, myoblasts, keratinocytes, endothelial cells, and bronchial epithelial cells.

EXAMPLES

The present invention is further described by the following examples. The examples are provided solely to illustrate the invention by reference to specific embodiments. These exemplifications, while illustrating certain specific aspects of the invention, do not portray the limitations or circumscribe the scope of the disclosed invention.

Certain terms used herein are explained in the foregoing glossary.

All examples are carried out using standard techniques, which are well known and routine to those of skill in the art, except where otherwise described in detail. Routine molecular biology techniques of the following examples can be carried out as described in standard laboratory manuals, such as Sambrook et al.

All parts or amounts set out in the following examples are by weight, unless otherwise specified.

Unless otherwise stated size separation of fragments in the examples below is carried out using standard techniques of agarose and polyacrylamide gel electrophoresis ("PAGE") as described in Sambrook and numerous other references such as Goeddel et al., *Nucleic Acids Res.*, 1980, 8: 4057.

Unless described otherwise, ligations are accomplished using standard buffers, incubation temperatures and times, approximately equimolar amounts of the DNA fragments to be ligated and approximately 10 units of T4 DNA ligase ("ligase") per 0.5 pg of DNA.

Example 1
Comparison of Myotrophin mRNA levels in normal vs. hypertrophied hearts Levels of myotrophin mRNA in normal and hypertrophied hearts are compared by Northern Blot analysis. Poly A+ mRNA is isolated from the hearts of control and diseased hearts according to standard procedures. These are then fractionated by electrophoresis on a denaturing formaldehyde/1.2% agarose gel and blotted onto a positively charged nylon membrane. The membrane is probed with the myotrophin cDNA which has been radiolabeled with $^{32}P$ using the appropriate hybridization conditions followed by high stringency washes. The signal generated is quantitated by phosphorimaging. Similar protocols are also employed to assess the levels of myotrophin in other tissues. For example, basal levels of myotrophin expression can be examined in various other vascular cells by Northern analysis, as well as the ability of various of factors including growth factors and cytokines to regulate its expression.

Example 2
Effect of Myotrophin on the activity of NF-κB

The effect of myotrophin overexpression on NF-κB is determined using a luciferase reporter gene which is under control of an NF-κB driven promoter. HSABH01 is cloned into the EcoRI(5')XhoI(3') sites of the mammalian expression vector pcDNA3+ (Invitrogen, San Diego, Calif.). pcDNA3myo is then transfected into a U937 human leukemia cell line which has been stably transfected with an IL-8 core promoter driven luciferase gene. The effect of myotrophin over-expression is then monitored by measuring luciferase activity.

Example 3
Effect of Myotrophin overexpression in cultured cells

Cultured cells transfected with the pcDNA3myo vector described in Example 3 using a calcium phosphate precipitation method. After 48 hours, cell size and area which are indicative of hypertrophy are assessed in accordance with procedures well known to those skilled in the art.

Example 4
Effect of Myotrophin overexpression on the activation of NF-κB in cardiac myocytes Control and myotrophin expressing cells are assessed for NF-κB activity by electrophoretic mobility shift assay. Nuclear and cytoplasmic extracts are prepared from the respective cells in accordance with procedures well known in the art. Nuclear (active) NF-κB is measured using a $^{32}P$ labeled oligonucleotide containing the consensus NF-κB DNA binding motif. The presence of a shifted band is indicative of activated NF-κB.

Example 5
Hypertrophy model.

We further confirmed in hearts obtained from a hypoxic chamber model of pulmonary hypertension, a model of right ventricular hypertrophy, that HSABH01 (or the human myotrophin/V-1) cDNA would detect elevated levels of myotrophin/V-1 mRNA in ventricular hypertrophy. Northern blot analysis of myotrophin/V-1 expression using the human cDNA probe against RNA from these hypertrophic hearts indicated that myotrophin/V-1 expression is correlated with ventricular hypertophy. Multiple bands were detected for rat myotrophin/V-1 as has been reported by others (Adihary et al., 1996; Sivasubramanian et al., 1996). Using the predominant 4.3 kb band, myotrophin/V-1 levels expressed as the ratio of myotrophin/V-1 hybridization signal intensity to GAPDH hybridization signal intensity to normalize for RNA loading variation increased from 0.46 0.034 at control to 1.0 0.024 at day 7 and 1.12 0.082 after 14 days hypoxia. All previous reports characterizing myotrophin expression in cardiac hypertrophy used models of left ventricular hypertrophy. The present data indicates that myotrophin/V-1 expression correlates with the degree of hypertrophy in a model of right ventricular hypertrophy, and suggests a role for myotrophin/V-1 in the hypertophy process independent of whether the right or left ventricle is involved.

What is claimed is:

1. An isolated polynucleotide having a nucleotide sequence encoding a polypeptide having the amino acid sequence of SEQ ID NO:2.

2. The isolated polynucleotide of claim 1 wherein the polynucleotide is DNA.

3. The isolated polynucleotide of claim 2 wherein said polynucleotide comprises the nucleotide sequence set forth in SEQ ID NO: 1.

4. The isolated polynucleotide of claim 1 wherein the polynucleotide is RNA.

5. The isolated polynucleotide of claim 1 wherein said polynucleotide consists of nucleotides 60 to 416 of the nucleotide sequence set forth in SEQ ID NO: 1.

6. The isolated polynucleotide of claim 1 having an RNA sequence corresponding to the entire nucleotide sequence set forth in SEQ ID NO:1.

7. The isolated polynucleotide of claim 1 having an RNA sequence corresponding to nucleotides 60 to 416 of the nucleotide sequence set forth in SEQ ID NO:1.

8. An expression vector comprising a polynucleotide which encodes the amino acid sequence set forth in SEQ ID NO:2.

9. A host cell comprising the expression vector of claim 8.

10. A process for producing a polypeptide having the amino acid sequence of SEQ ID NO:2, the process comprising culturing the host cell of claim 9 under conditions sufficient for the production of said polypeptide and recovering said polypeptide from the culture.

11. A process for producing a cell which produces a polypeptide having the amino acid sequence set forth in SEQ ID NO:2, the process comprising transforming or transfecting a host cell with the expression vector of claim 8 such that the host cell, under appropriate culture conditions, produces said polypeptide.

12. A recombinant host cell produced by the process of claim 11, expressing a polypeptide having the amino acid sequence set forth in SEQ ID NO:2.

13. An isolated polynucleotide which is complementary to a polynucleotide encoding the amino acid sequence of SEQ ID NO:2.

14. The isolated polynucleotide of claim 13 having a nucleotide sequence which is complementary to nucleotides 60 to 416 of the nucleotide sequence set forth in SEQ ID NO: 1.

* * * * *